United States Patent
Liu et al.

(10) Patent No.: US 7,829,839 B2
(45) Date of Patent: Nov. 9, 2010

(54) OPTICAL TWEEZERS LIFTING APPARATUS

(75) Inventors: Cheng-Hsien Liu, 8F., No. 305, Sec. 2, Guangfu Rd., East District, Hsinchu City (TW) 300; William Wang, Taoyuan (TW); Long Hsu, 18 Fl.-3, No. 25, Jianjhong 1st Rd., 25th Neighborhood, Feng-Gung Li, Eastern District, Hsinchu City (TW) 300; Chung-Cheng Chou, Taoyuan County (TW); Sheng-Yang Tseng, Hsinchu County (TW); Chen Peng, Taipei (TW); Fung-Hsu Wu, Taoyuan County (TW); Ta-Yuan Lee, Taipei County (TW)

(73) Assignees: Raydium Semiconductor Corp., Hsinchu (TW); Long Hsu, Hsinchu (TW); Cheng-Hsien Liu, Hsinchu (TW)

( * ) Notice: Subject to any disclaimer, the term of this patent is extended or adjusted under 35 U.S.C. 154(b) by 252 days.

(21) Appl. No.: 12/285,958

(22) Filed: Oct. 17, 2008

(65) Prior Publication Data
US 2010/0108872 A1 May 6, 2010

(30) Foreign Application Priority Data
Oct. 19, 2007 (TW) .............................. 96139402 A

(51) Int. Cl.
*H05H 3/00* (2006.01)
*C25B 9/16* (2006.01)

(52) U.S. Cl. ................. 250/251; 204/643; 210/270; 359/509; 359/558; 359/629

(58) Field of Classification Search ............... 250/251; 204/643; 210/270; 359/558, 509, 629
See application file for complete search history.

(56) References Cited

U.S. PATENT DOCUMENTS

| 2004/0262210 A1* | 12/2004 | Westervelt et al. | 210/222 |
| 2008/0174870 A1* | 7/2008 | Hsu et al. | 359/558 |
| 2009/0032692 A1* | 2/2009 | Hsu et al. | 250/251 |
| 2009/0040620 A1* | 2/2009 | Peng et al. | 359/629 |
| 2009/0233327 A1* | 9/2009 | Lau et al. | 435/29 |

* cited by examiner

*Primary Examiner*—Nikita Wells
(74) *Attorney, Agent, or Firm*—Bacon & Thomas, PLLC

(57) ABSTRACT

An optical tweezers lifting apparatus is provided. The optical tweezers lifting apparatus includes an optical tweezers and a particle-lifting device. The particle-lifting device includes a substrate and a plurality of electrodes that are disposed on the bottom of a flow path in the substrate. When a dielectrophoresis (DEP) solution with a plurality of floating particles is conducted into the flow path and upon those electrodes and a voltage is applied to these electrodes, these particles would be driven by a negative DEP force to move upward to a specific depth in the flow path. Meanwhile, the optical tweezers of the apparatus is selectively focused at the specific depth in the flow path.

15 Claims, 6 Drawing Sheets

US 7,829,839 B2

OPTICAL TWEEZERS LIFTING APPARATUS

This application claims the benefit of Taiwan application Serial No. 96139402, filed Oct. 19, 2007, the subject matter of which is incorporated herein by reference.

BACKGROUND OF THE INVENTION

1. Field of the Invention

The invention relates in general to an optical tweezers lifting apparatus using the same, and more particularly to an optical tweezers lifting apparatus using dielectrophoresis (DEP) technology.

2. Description of the Related Art

In the fields of micro electro mechanical system (MEMS), nanometer (nano) technology and biomedicine, the existing technologies can hardly process a single micro particle such as nanometer molecule, protein, cell or virus. With rapid advance in material science and manufacturing technology, many micro-systems used in controlling micro particles are now developed. These micro-systems are mostly used in the inspection, separation or selection of particles. However, since the manufacturing process of these micro-systems is very complicated and the to-be-processed particles are too small, there are still many problems in the practical operation of the micro-systems.

Optical tweezers technology has great advantage in the control of μm level particles. Normally, a single laser beam is focused to control the particles via the variation of photon momentum. Due to the non-mechanical and non-destructive property of the light, the optical tweezers technology is widely used in the fields such as MEMS, nanometer technology and biomedicine. However, the optical tweezers is capable of controlling the particles on the focal plane by focusing with a laser beam but the optical tweezers still cannot guarantee that all the particles sent in are located on the focal plane. Thus, the optical tweezers cannot effectively control the particles.

SUMMARY OF THE INVENTION

The invention is directed to an optical tweezers lifting apparatus. The optical tweezers lifting apparatus of the invention is widely used in the fields such as micro electro mechanical system, nanometer technology and biomedicine for inspecting, lifting or sorting micro particles.

According to a first aspect of the present invention, a particle-lifting device including a substrate and a plurality of electrodes is provided. These electrodes are disposed on the bottom of a flow path in the substrate. When a dielectrophoresis (DEP) solution with a plurality of floating particles is conducted into the flow path and upon those electrodes and a voltage is applied to these electrodes, these particles would be driven by a negative DEP force to move upward to a specific depth in the flow path.

According to a second aspect of the present invention, an optical tweezers lifting apparatus including an optical tweezers and a particle-lifting device is provided. The particle-lifting device includes a substrate and a plurality of electrodes that are disposed on the bottom of a flow path in the substrate. When a dielectrophoresis (DEP) solution with a plurality of floating particles is conducted into the flow path and upon those electrodes and a voltage is applied to these electrodes, these particles would be driven by a negative DEP force to move upward to a specific depth in the flow path. The optical tweezers can be selectively focused at the specific depth in the specific depth of the flow path.

The invention will become apparent from the following detailed description of the preferred but non-limiting embodiments. The following description is made with reference to the accompanying drawings.

DETAILED DESCRIPTION OF THE INVENTION

First Embodiment

Figure 1A:
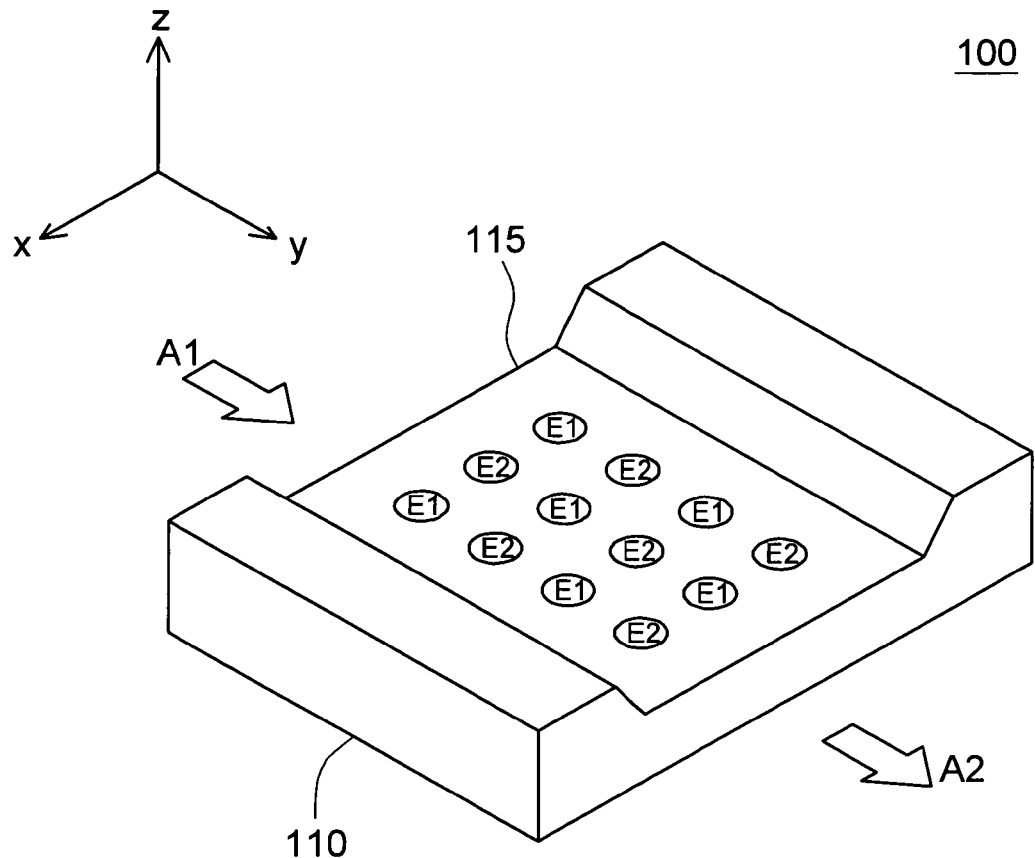
FIG. 1A is a diagram of a particle-lifting device according to a first embodiment of the invention.
Figure 1B:
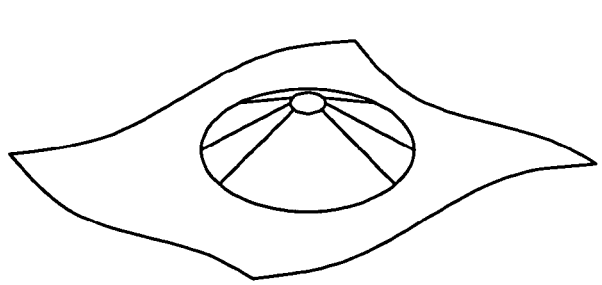
FIG. 1B is a 3-D diagram of the electrode in FIG. 1A.

FIG. 1A is a diagram of a particle-lifting device according to a first embodiment of the invention. FIG. 1B is a 3-D diagram of the electrode in FIG. 1A. As shown in FIG. 1A, the particle-lifting device 100 includes a substrate 110 and a plurality of electrodes that are disposed on the bottom of a flow path 115 in the substrate 110. When a dielectrophoresis (DEP) solution with a plurality of floating particles is conducted into the flow path 115 and upon those electrodes and a voltage is applied to these electrodes, these particles would be driven by a negative DEP force to move upward to a specific depth in the flow path 115.

The electrodes on the substrate 110 can be divided into two groups of electrodes with opposite electric property, such that an electric field is generated when a voltage is applied to these electrodes. As shown in FIG. 1A, there are first electrodes E1 and second electrodes E2 disposed on the substrate 110, and when a voltage is applied to the first electrodes E1 and the second electrodes E2, the electric property of the first electrodes E1 is opposite to that of the second electrodes E2. Preferably, the first electrodes E1 and the second electrodes E2 are alternately disposed on the flow path 115. As shown in FIG. 1B, each of the above electrodes is, for example, a pyramid structure.

The DEP solution is conducted into the flow path 115 in the direction A1 and is drained from the flow path 115 in the direction A2. The DEP solution has a plurality of particles. In order to generate a negative DEP force to drive the particles, the conductivity coefficient of the DEP solution is substantially larger than that of the particles. Thus, when an electric field is produced, the polarization of the DEP solution is greater than that of the particles, such that the particles move towards where the electric field intensity is small. How the present embodiment of the invention lifts the particles by the negative DEP force is disclosed in the exhibits below.

Figure 2A:
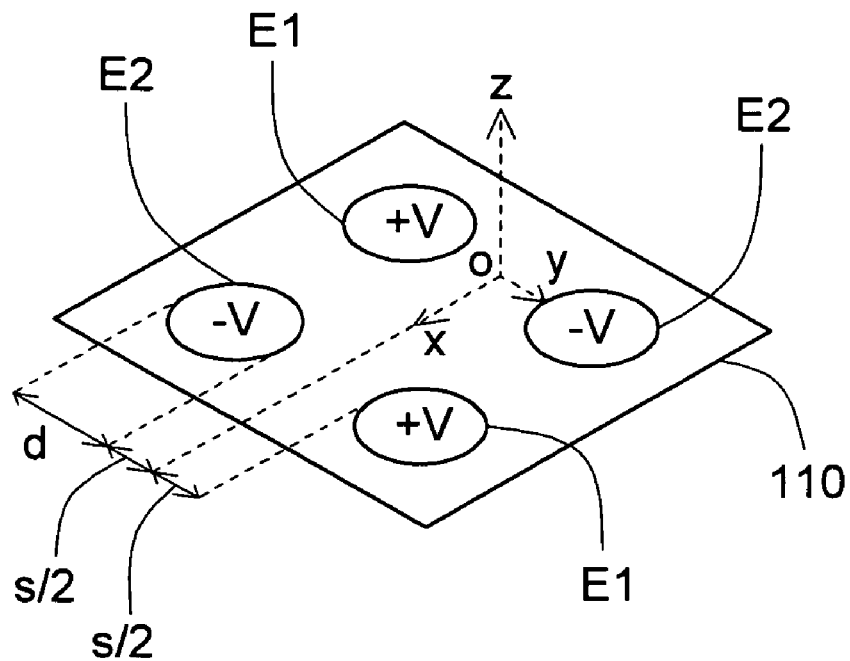
FIG. 2A is a diagram showing a part of the electrodes in FIG. 1A disposed on a substrate.
Figure 2B:
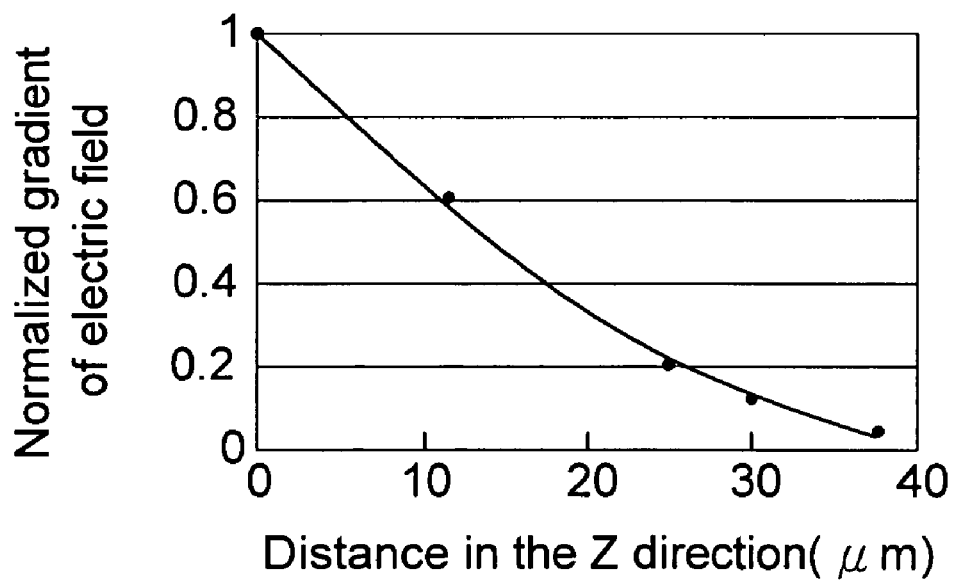
FIG. 2B is a gradient diagram showing the electric field generated by the electrodes of FIG. 2A in the Z direction.

FIG. 2A is a diagram showing a part of the electrodes in FIG. 1A disposed on the substrate. FIG. 2B is a gradient diagram showing the electric field generated by the electrodes of FIG. 2A in the Z direction. As shown in FIG. 2A, the diameter d of an electrode is about 10 μm, and the gap S between two neighboring electrodes is about 50 μm. Each first electrode E1 and each second electrode E2 are connected to an AC power whose applied voltage frequency is about 1 million Hz (MHz). As shown in FIG. 2B (after normalization), with the above parameters of the electrodes being used and the distribution of electric field being observed along the Z direction, the intensity of the electric field generated in the flow path 115 by the first electrodes E1 and the second electrodes E2 decreases as the distance to the bottom of the substrate 110 increases (the position of the bottom of the flow path 115 is denoted as Z=0). In other words, the farther away from the bottom of the flow path 115, the smaller the intensity of the electric field generated by the electrodes E1 and E2 will be.

Figure 3A:
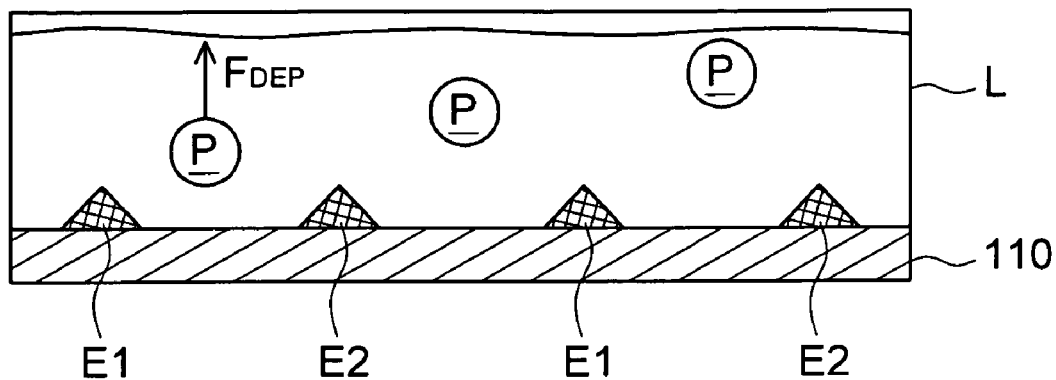
FIG. 3A is a diagram showing the sectional view of the flow path in FIG. 1A with the conduction of a solution.
Figure 3B:
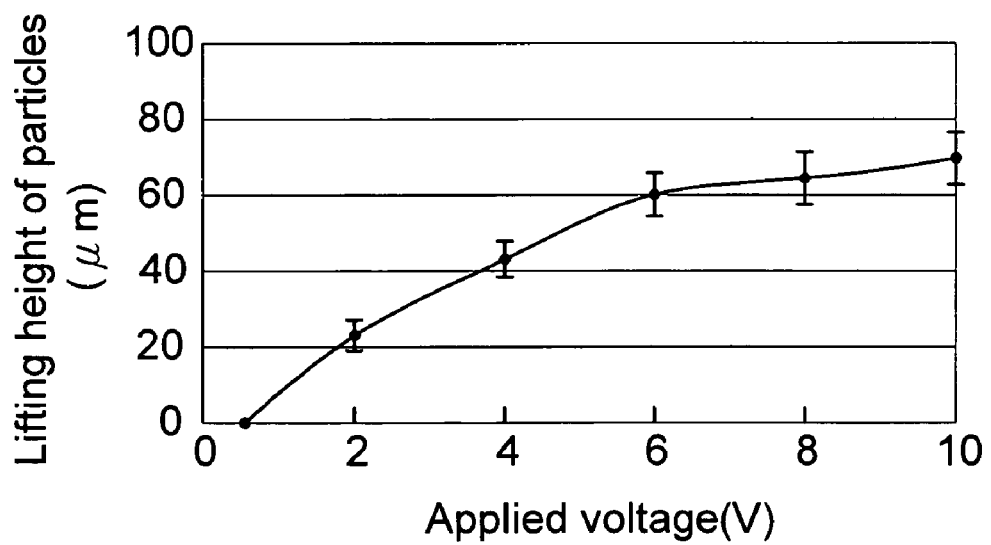
FIG. 3B is a diagram showing the relationship diagram of the applied voltage in FIG. 3A with the lifting height of particles.

FIG. 3A is a diagram showing the sectional view of the flow path in FIG. 1A with the conduction of a solution. FIG. 3B is a diagram showing the relationship of the applied voltage in FIG. 3A with the lifting height of particles. The diameter of the particles P in the present embodiment of the invention is about 10 μm, wherein the particles are latex particles, and the DEP solution L is a de-ionized water solution. Other properties of the particles P and the DEP solution L are illustrated in Table 1.

TABLE 1

|  | Dielectric Constant | Conductivity Coefficient |
| --- | --- | --- |
| De-Ionized Water | 80 | 1.3E−4 |
| Particles | 7 | 1.0E−12 |

As the conductivity coefficient of the de-ionized solution is far larger than that of the latex particles, when the electrodes E1 and E2 are conducted to generate an electric field, the polarization degree of the de-ionized solution will be greater than that of the latex particles. Thus, a negative DEP force $F_{DEP}$ is generate to the particles P, so as to move the particles P towards where the electric field intensity is small. As shown in FIG. 3A, the farther away a location from the bottom of the substrate 110 is, the smaller the intensity of the electric field is, so the particles P will be gradually lifted during the movement process. Furthermore, as shown in FIG. 3B, the larger applied voltage the electrodes E1 and E2 have, the greater the intensity of the electric field generated by the electrodes E1 and E2 is, and the higher the particles P are lifted. According to the above properties, after the particles P enter the flow path 115, the user can control the lifting height of the particles P by adjusting the magnitude of the applied voltage.

The diameter of the particles P is 10 μm in the above disclosure. However, the particle-lifting device 100 in the present embodiment of the invention is not limited by the size of the particles. The negative DEP force is related to the factors such as the size of the particles, the dielectric constant of the solution, and the intensity of the electric field. During the process of lifting the particles, the negative DEP force has to overcome the gravity of the particles, which can be expressed in an equation. As both the negative DEP force and the gravity of the particles are related to the volume of the particles, the same factor such as the diameter of the particles is eliminated in the equation, the lifting effect is therefore not affected by the size of the particles. That is, although the particles in the solution may have different sizes, all particles still can be lifted to the same height in the flow path 115 under the same applied voltage.

The first embodiment is illustrated by the de-ionized solution and latex particles. However, the particle-lifting device 100 in the present embodiment of the invention also can be applied to lift or sort other types of particles as long as appropriate solution is selected considering the property of the particles.

The particle-lifting device 100 in the present embodiment of the invention is applicable to lifting the particles of various types and sizes. By adjusting the magnitude of the applied voltage, the particle-lifting device 100 in the present embodiment of the invention can lift the particles to different depths in the flow path, facilitating the following procedure of processing the particles. For example, when the particle-lifting device 100 in the present embodiment of the invention is applied to an optical tweezers, the control problem of the particles, which arises as the laser beam is focused at a wrong position, is effectively resolved since the lifting height of the particles can be controlled. In addition, if an inspecting step is incorporated, the particle-lifting device 100 of the present embodiment of the invention is capable of selecting particular particles. The selecting process is elaborated below with accompanying drawings.

Figure 4:
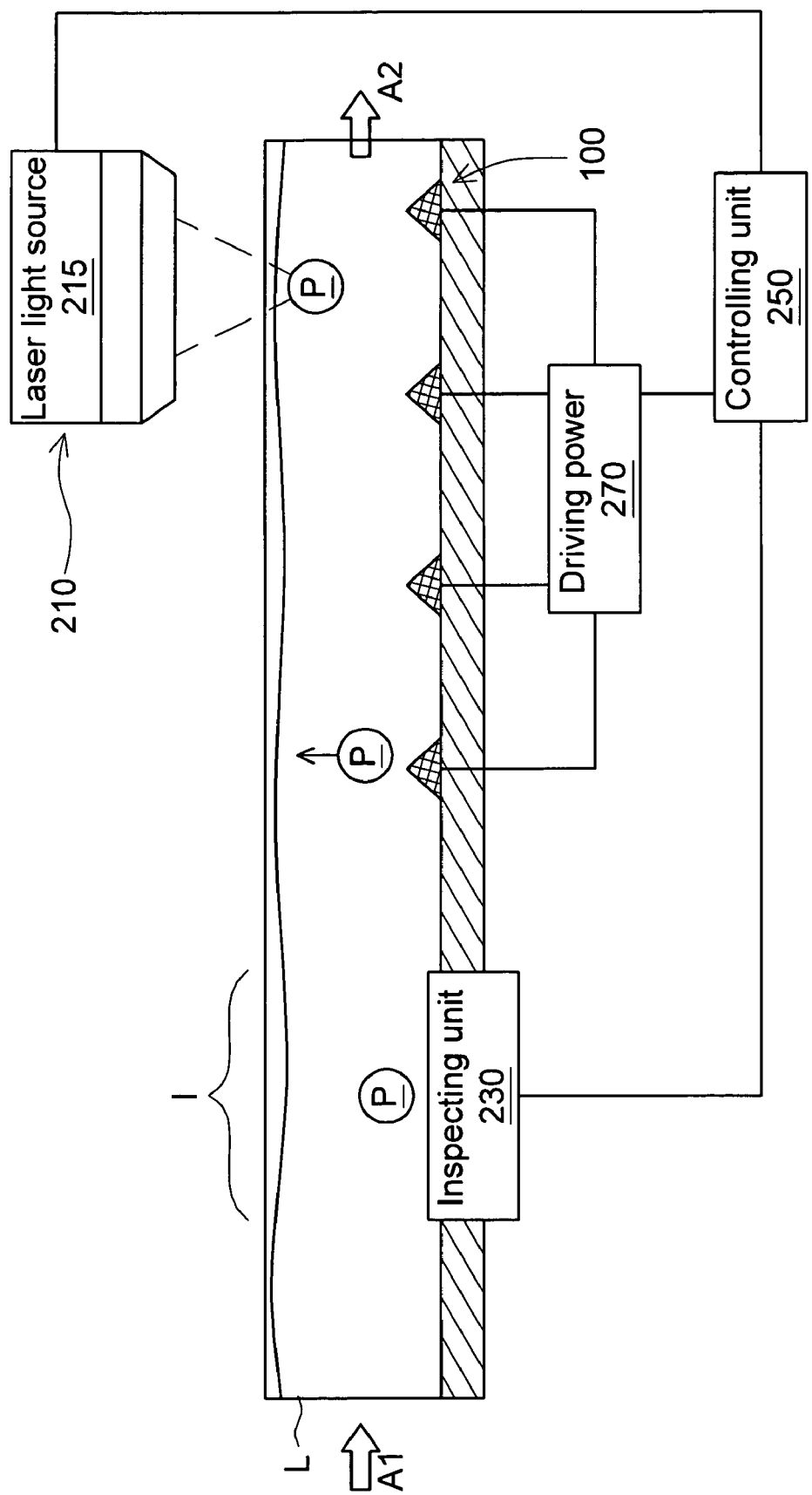
FIG. 4 is a diagram showing an optical tweezers lifting apparatus according to the first embodiment of the invention.

FIG. 4 is a diagram showing an optical tweezers lifting apparatus according to the first embodiment of the invention. As shown in FIG. 4, the optical tweezers lifting apparatus 200 includes an optical tweezers 210, an inspecting unit 230, a controlling unit 250 and a particle-lifting device 100. The controlling unit 250 is electrically connected to the laser light source 215 of the optical tweezers 210, the inspecting unit 230 and the driving power 270 of the particle-lifting device 100. The inspecting unit 230 is used for inspecting particles and can be implemented by an image sensing device, a photo-electro sensing device, an appliance sensing device, a magnetism sensing device or the combination of the above sensing devices. The inspecting unit 230 is capable of recognizing the properties of articles according to different items of property, for example, the recognition of particle image by the image sensing device, the deflection/scattering matching of particles by the photo-electro sensing device, the conductivity/dielectricity matching of particles by the appliance sensing device, and the magnetic effect (magnetic flux) matching of particles by the magnetism sensing device.

As for the particle-lifting device 100, the lifting height of the particles P is adjusted by controlling the applied voltage of the electrodes. In addition, the particle-lifting device 100 is incorporated with the optical tweezers 210, such that after the particles P are lifted, the particles P are exactly located at where the laser beam is focused, hence effectively resolving the conventional problem that the particles P cannot be located at where the optical tweezers 210 is focused.

The DEP solution L with particles P is conducted into the flow path (arrow A1) via a micro-pump (not illustrated) from a particle storage cave (not illustrated), for example. Firstly, the particles P pass through an inspecting area I to be inspected by the inspecting unit 230. After the particles P are inspected by the inspecting unit 230, the subsequent processing is determined according to the purpose of the optical tweezers lifting apparatus 200. For example, if the purpose is to select the particles P having a particular property from the particle storage cave, the inspecting unit 230 will send a signal to the controlling unit 250 after the particles P are inspected, and the controlling unit 250 will determine whether the particles P are the desired particles. If confirmed, the controlling unit 250 continues to activate the lifting mechanism of the particle-lifting device 100. The controlling unit 250 activates the driving power (AC power) 270 according to the inspecting data of the particles P and applies the right voltage to each electrode so as to generate a corresponding uneven electric field. When the particles P enter the particle-lifting device 100, the particles P would be driven by a negative DEP force to move upward. As the particles P are lifted to a specific height, the optical tweezers 210 will hold the particles P for further processing. Thus, only the selected particles will enter the lifting procedure, and the remaining particles will leave the flow path along the direction A2.

Alternatively, the particles are sorted by the optical field of the optical tweezers 210. As shown in FIG. 4, after the particles P enter the optical tweezers lifting apparatus 200 from the particle storage cave, whenever the inspecting unit 230 detects that a particle P exists, the inspecting unit 230 will send a signal to the controlling unit 250. The controlling unit 250 immediately starts the lifting mechanism when receiving the signal. As disclosed above, the lifting mechanism of the particle-lifting device 100 is not affected by the size of the particles, therefore all particles are effectively lifted to a specific height that the focal plane of the optical tweezers 210 is, and then the particles are sorted by the optical tweezers 210. At present, the technology of the optical tweezers 210 enables the laser beam to form an optical field that has a plurality of guiding lines on the focal plane. These guiding lines are designed according to different properties of the particles. For example, larger-sized particles will result in larger deflection effect, so that the particles can be sorted according to the deflection of the particle.

According to the optical tweezers technology used in the present embodiment of the invention, the diffractive optical element in the optical path can be adjusted by a computer or a similar computer processing unit so as to generate a desired optical field. The data of the above inspecting mechanism, the particle-lifting mechanism and the optical path of the optical tweezers lifting apparatus can be integrated in one single processing unit (for example, located in the controlling unit 250). Thus, a better mechanism for the sample to be handled can be provided so as to increase the operating effect.

Second Embodiment

Figure 5A:
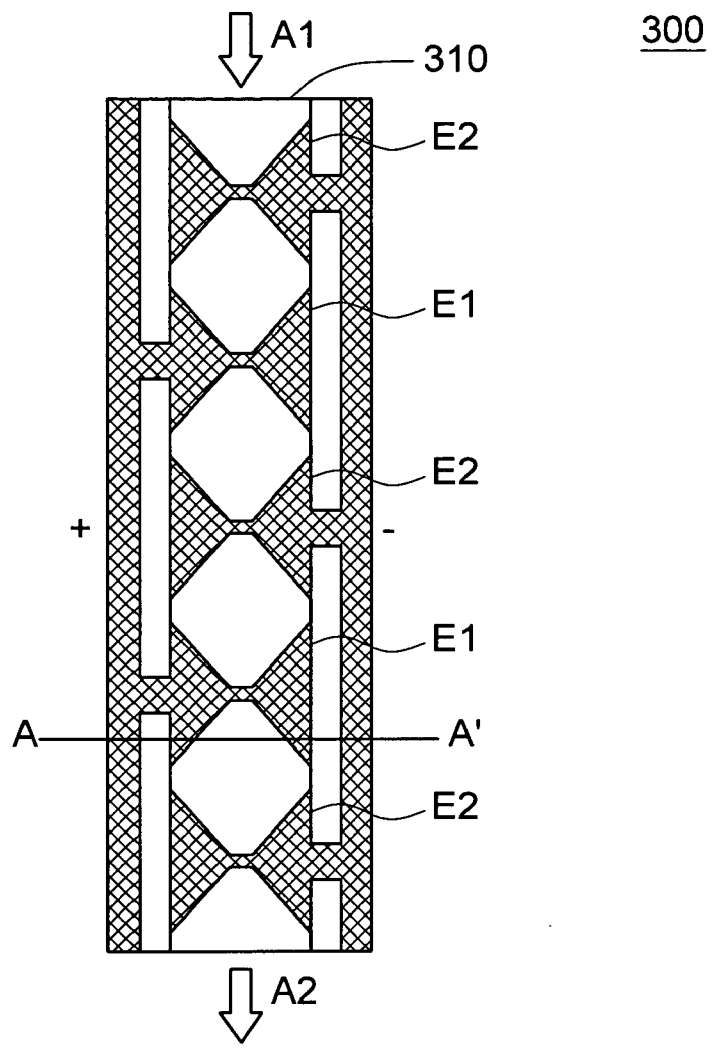
FIG. 5A is a diagram showing a particle-lifting device according to a second embodiment of the invention.
Figure 5B:
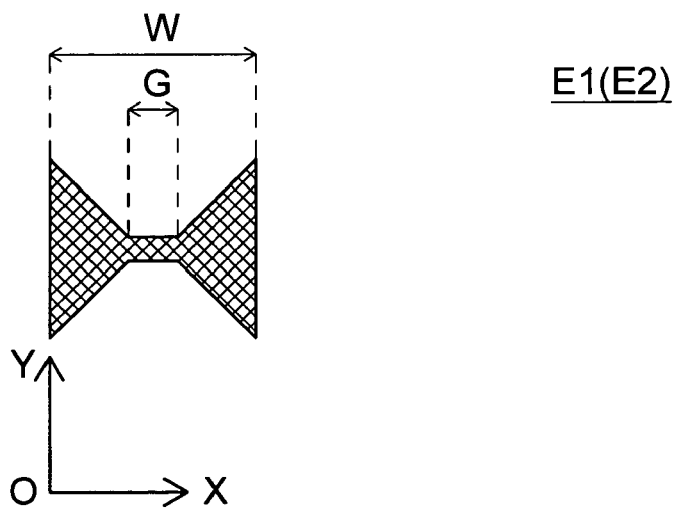
FIG. 5B is a diagram showing a single electrode in FIG. 5A.

FIG. 5A is a diagram showing a particle-lifting device according to a second embodiment of the invention. FIG. 5B is a diagram showing a single electrode in FIG. 5A. As shown in FIG. 5A, a plurality of electrodes are disposed on a substrate 310 of the particle-lifting device 300, wherein these electrodes include first electrodes E1 and second electrodes E2 whose electric property is opposite to that of the first electrodes E1. All first electrodes E1 are inter-connected and so are all second electrodes E2 inter-connected, such that all of the first electrodes E1 or the second electrodes E2 have the same electric property and the same magnitude of voltage when the first electrodes E1 or the second electrodes E2 are driven. The first electrodes E1 and the second electrodes E2 are disposed alternately such that an uneven electric field is generated on the substrate 310 when a voltage is applied to the electrodes E1 and E2.

Figure 6:
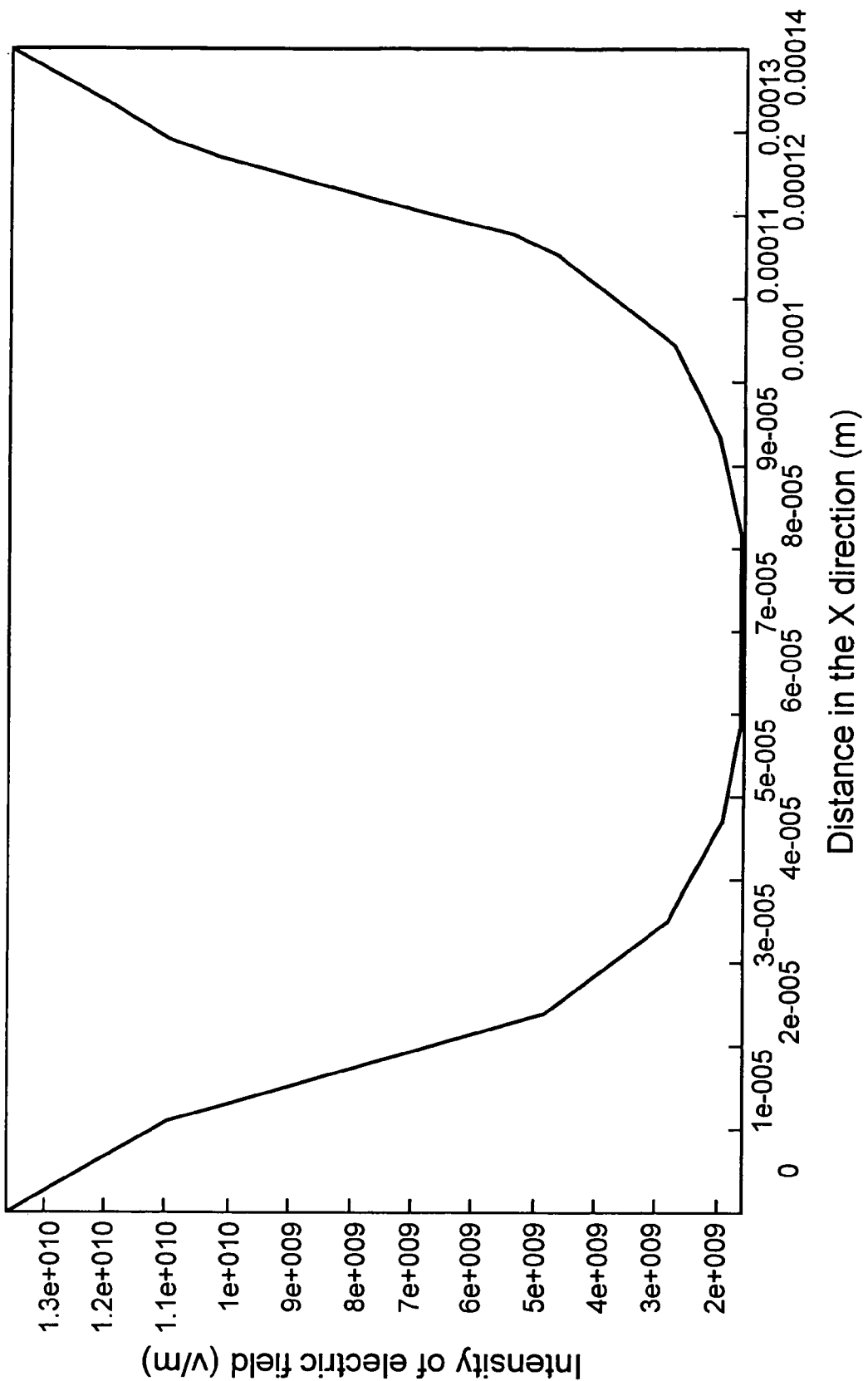
FIG. 6 is a diagram of the distribution of the simulated electric field along the cross-sectional line A-A' in FIG. 5A.

As shown in FIG. 5B, each of the electrodes E1 and E2 is a plate structure, and two tips of each electrode are connected such that each electrode looks like a butterfly. In the experiment of the present embodiment of the invention, the width W of each electrode is about 140 μm, and the gap G between two tips of each electrode is about 20 μm, the applied voltage ranges between 0 and 10 V and the driving frequency ranges between 1 to 100 Hz. With the above parameters, a diagram of the distribution of the simulated electric field along the cross-sectional line A-A' in FIG. 5A is shown in FIG. 6. In the present embodiment of the invention, the latex particles with the diameter of about 10 μm are mixed with the de-ionized solution. Other properties of the particles and the de-ionized water are illustrated in Table 1.

As shown in FIG. 6, when the distance in the X direction (the X direction and the Y direction are defined in FIG. 5B) increases, the electric field intensity decreases. After the electric field intensity decreases to the lowest intensity, the electric field intensity will turn to increase gradually. Referring to FIG. 5A or FIG. 5B, when a voltage is applied to the electrodes E1 and E2, the electric field at the central part of the substrate 310 has the smallest intensity (corresponding to the connection of the tips of each electrode). The experimental results of the particle-lifting device 300 are illustrated in Exhibits 1 and 2. In the experiment, particles are released to the flow path from three different locations on the substrate 310 to move in the direction A1 and then to leave the flow path in the direction A2. The particles on the three different locations of Exhibits 1 and 2 are shown in blue color, green color and red color, and the blocks in different colors on the substrate 310 represent different levels of the electric field intensity. As shown in Table 1, since the conductivity coefficient of the latex particles is far smaller than that of the de-ionized solution, the particles have little degree of the polarization. Therefore, the particles in the electric field would be driven by a negative DEP force to move towards where the electric field intensity is small. As indicated in the steps 1 to 10 of the Exhibits 1 and 2, the particles are released from three different positions but will be gradually moved to the central part of the substrate 310 where the electric field has the smallest intensity along with the flow of the de-ionized solution.

Consequently, the particle-lifting device 300 generates a trapping-like effect on the particles in the flow path such that the particles are sorted and the subsequent processing of the particles is made easier. The particle-lifting device 300 in the present embodiment of the invention can be equipped with an inspecting unit to inspect the properties of the particles. As the particles are moved forward sequentially, the problem that several particles pass through the inspecting unit at the same time is solved, and the erroneous judgment of the inspecting unit when many particles pass through the inspecting unit at the same time will is avoided accordingly. Besides, when the particles are moved forward in sequence, the counting of the particle number is made easier.

The particle-lifting mechanism and the optical tweezers technology disclosed in the first and the second embodiments can be widely applied to the fields such as micro electro mechanical system, nanometer technology or biomedicine. For example, the technology of the invention can be used for the compositions of the blood or body fluid such as counting and sorting different cells in the blood, or filtering the impurities or particles in the body fluid.

According to the particle-lifting device and the optical tweezers lifting apparatus using the same disclosed in the above embodiments of the invention, when a voltage is applied to the electrodes disposed on the bottom of the flow path of a substrate, an uneven electric field is generated. Since the polarization degree of the particles is different from that of the solution, the particles would be driven by a negative DEP force to move upward. The optical tweezers is capable of entrapping the particles at particular position in the flow path for subsequent processing. In addition, with appropriate shape and disposition of the electrodes, the particles will be moved in sequence in the flow path and make the subsequent processing of particles easier.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A particle-lifting device, comprising:
a substrate having a flow path, wherein a dielectrophoresis (DEP) solution with a plurality of floating particles are conducted into the flow path; and
a plurality of electrodes disposed on the substrate and located on the bottom of the flow path, wherein when a voltage is applied to the electrodes, an electric field is generated on the substrate such that when the particles flow through the electrodes with the DEP solution, the particles are driven by a negative DEP force to move upward to a specific depth in the flow path.

2. The particle-lifting device according to claim 1, wherein the conductivity coefficient of the particles is substantially smaller than the conductivity coefficient of the DEP solution.

3. The particle-lifting device according to claim 1, wherein when the voltage of the electrodes is adjusted, the negative DEP force applied to the particles is changed such that the depth of the particles in the flow path changes accordingly.

4. The particle-lifting device according to claim 1, wherein each electrode is a pyramid structure.

5. The particle-lifting device according to claim 1, wherein the electrodes comprises a plurality of first electrodes and a plurality of second electrodes whose electric property is opposite to that of the first electrodes.

6. The particle-lifting device according to claim 5, wherein the first electrodes and the second electrodes are disposed alternately.

7. An optical tweezers lifting apparatus, comprising:
an optical tweezers; and
a particle-lifting device, comprising:
a substrate having a flow path, wherein a DEP solution with a plurality of floating particles is conducted into the flow path; and
a plurality of electrodes disposed on the substrate and located on the bottom of the flow path, wherein when a voltage is applied to the electrodes, an electric field is generated on the substrate such that when the particles flow through the electrodes with the DEP solution, the particles are driven by a negative DEP force to move upward to a specific depth in the flow path and the optical tweezers is selectively focused at the specific depth in the flow path.

8. The optical tweezers lifting apparatus according to claim 7, wherein the conductivity coefficient of the particles is substantially smaller than that of the DEP solution.

9. The optical tweezers lifting apparatus according to claim 7, wherein when the voltage of the electrodes is adjusted, the negative DEP force applied to the particles is changed such that the depth of the particles in the flow path changes accordingly.

10. The optical tweezers lifting apparatus according to claim 7, wherein each electrode is a pyramid structure.

11. The optical tweezers lifting apparatus according to claim 7, wherein the electrodes comprises a plurality of first electrodes and a plurality of second electrodes whose electric property is opposite to that of the first electrodes.

12. The optical tweezers lifting apparatus according to claim 11 s, wherein the first electrodes and the second electrodes are disposed alternately.

13. The optical tweezers lifting apparatus according to claim 7, wherein the laser focal point of the optical tweezers is substantially located at a specific depth in the flow path.

14. The optical tweezers lifting apparatus according to claim 7, further comprising:
an inspecting unit for inspecting the properties of the particles, wherein the particle-lifting device adjusts the lifting height of the particles by controlling the applied voltage of the electrodes according to the properties of the particles.

15. The optical tweezers lifting apparatus according to claim 14, wherein the inspecting unit is an image sensing device, a photo-electro sensing device, an appliance sensing device, a magnetism sensing device or a combination of at least two of the above sensing devices.

* * * * *